(12) United States Patent
Gao et al.

(10) Patent No.: US 10,079,183 B2
(45) Date of Patent: Sep. 18, 2018

(54) CALCULATED ELECTRICAL PERFORMANCE METRICS FOR PROCESS MONITORING AND YIELD MANAGEMENT

(71) Applicant: KLA-Tencor Corporation, Milpitas, CA (US)

(72) Inventors: Xiang Gao, San Jose, CA (US); Philip D. Flanner, III, Union City, CA (US); Leonid Poslavsky, Belmont, CA (US); Ming Di, Hayward, CA (US); Qiang Zhao, Milpitas, CA (US); Scott Penner, Livermore, CA (US)

(73) Assignee: KLA-Tenor Corporation, Milpitas, CA (US)

( * ) Notice: Subject to any disclaimer, the term of this patent is extended or adjusted under 35 U.S.C. 154(b) by 809 days.

(21) Appl. No.: 14/312,568

(22) Filed: Jun. 23, 2014

(65) Prior Publication Data
US 2015/0006097 A1    Jan. 1, 2015

Related U.S. Application Data

(60) Provisional application No. 61/839,708, filed on Jun. 26, 2013.

(51) Int. Cl.
*G01N 21/21* (2006.01)
*H01L 21/66* (2006.01)

(52) U.S. Cl.
CPC ............ *H01L 22/12* (2013.01); *G01N 21/211* (2013.01); *H01L 22/20* (2013.01); *G01N 2021/213* (2013.01)

(58) Field of Classification Search
CPC ..... H01L 22/12; H01L 22/20; G01N 21/2112; G01N 2021/213
See application file for complete search history.

(56) References Cited

U.S. PATENT DOCUMENTS 6,465,265 B2    10/2002  Opsal et al.
6,694,284 B1 *   2/2004  Nikoonahad ........ G01N 21/211
                                                              702/155

(Continued)

FOREIGN PATENT DOCUMENTS

CN    101853797 A  * 10/2010 ......... G01N 21/8806
JP    2008235323        10/2008
WO    2007059080 A2     5/2007

OTHER PUBLICATIONS

International Search Report and Written Opinion dated Oct. 13, 2014, for PCT Application No. PCT/US2014/044148 filed on Jun. 25, 2014, by KLA-Tencor Corporation, 11 pages.

(Continued)

*Primary Examiner* — Mischita Henson
(74) *Attorney, Agent, or Firm* — Spano Law Group; Joseph S. Spano

(57) ABSTRACT

Methods and systems of process control and yield management for semiconductor device manufacturing based on predictions of final device performance are presented herein. Estimated device performance metric values are calculated based on one or more device performance models that link parameter values capable of measurement during process to final device performance metrics. In some examples, an estimated value of a device performance metric is based on at least one structural characteristic and at least one band structure characteristic of an unfinished, multi-layer wafer. In some examples, a prediction of whether a device under process will fail a final device performance test is based on the difference between an estimated value of a final device performance metric and a specified value. In some examples, an adjustment in one or more subsequent process steps is determined based at least in part on the difference.

19 Claims, 6 Drawing Sheets

(56) References Cited

U.S. PATENT DOCUMENTS

| | | |
|---|---|---|
| 7,239,391 B2 | 7/2007 | Synowicki et al. |
| 7,414,721 B1 | 8/2008 | Suvkhanov et al. |
| 2002/0045282 A1 | 4/2002 | Opsal et al. |
| 2010/0068834 A1* | 3/2010 | Hachigo .............. G01N 21/211 438/16 |
| 2010/0165340 A1* | 7/2010 | Xu ..................... G01B 11/0641 356/327 |
| 2012/0021539 A1 | 1/2012 | Allenic et al. |
| 2013/0083320 A1 | 4/2013 | Gao et al. |

OTHER PUBLICATIONS

He, G., et al, "Thickness-modulated Optical Dielectric Constants and Band Alignments of HfOxNy Gate Dielectrics," Journal of Applied Physics, Jan. 14, 2009, 105, 014109, pp. 1-4, USA.

Price, J., et al., "Identification of Interfacial Defects in High-k Gate Stack Films By Spectroscopic Ellipsometry," Journal of Vacuum Science and Technology, American Vacuum Society, Feb. 9, 2009, B 27(1), pp. 310-312, USA.

Price, J., et al., "Identification of Sub-Band-Gap Absorption Features At the HfO2/Si(100) Interface Via Spectroscopic Ellipsometry," Applied Physics Letters, American Institute of Physics, Aug. 10, 2007, 91, 061925, pp. 1-3, USA.

International Search Report and Written Opinion dated Mar. 6, 2013, for PCT Application No. PCT/US2012/057019 filed on Sep. 25, 2012, by KLA-Tencor Corporation, 6 pages.

* cited by examiner

CALCULATED ELECTRICAL PERFORMANCE METRICS FOR PROCESS MONITORING AND YIELD MANAGEMENT

CROSS REFERENCE TO RELATED APPLICATION

The present application for patent claims priority under 35 U.S.C. § 119 from U.S. provisional patent application Ser. No. 61/839,708, entitled "Semiconductor Chip Fabrication Process Monitoring and Yield Management Through Calculated Electrical Performance Metrics," filed Jun. 26, 2013, the subject matter of which is incorporated herein by reference in its entirety.

TECHNICAL FIELD

The described embodiments relate to systems for wafer inspection and metrology, and more particularly to characterization and defect detection of semiconductor structures and materials used in semiconductor manufacturing.

BACKGROUND INFORMATION

Semiconductor devices such as logic and memory devices are typically fabricated by a sequence of processing steps applied to a substrate or wafer. The various features and multiple structural levels of the semiconductor devices are formed by these processing steps. For example, lithography among others is one semiconductor fabrication process that involves generating a pattern on a semiconductor wafer. Additional examples of semiconductor fabrication processes include, but are not limited to, chemical-mechanical polishing, etch, deposition, and ion implantation. Multiple semiconductor devices may be fabricated on a single semiconductor wafer and then separated into individual semiconductor devices.

Inspection processes are used at various steps during a semiconductor manufacturing process to detect defects on wafers to promote higher yield. As design rules and process windows continue to shrink in size, inspection systems are required to capture a wider range of physical defects on wafer surfaces while maintaining high throughput.

Semiconductor devices are increasingly valued based on their energy efficiency, rather than speed alone. For example, energy efficient consumer products are more valuable because they operate at lower temperatures and for longer periods of time on a fixed battery power supply. In another example, energy efficient data servers are in demand to reduce their operating costs. As a result, there is a strong interest to reduce the energy consumption of semiconductor devices.

In one example, leakage current through insulator layers is a major energy loss mechanism of semiconductor devices manufactured at the 65 nm technology node and below. In response, electronic designers and manufacturers are adopting new materials (e.g., hafnium silicate (HfSiO4), nitrided hafnium silicates (HfSiON), hafnium dioxide (HfO2), zirconium silicate (ZrSiO4), etc.) with higher dielectric constants and lower extinction coefficients than traditional materials (e.g., silicon dioxide). These "high-k" materials reduce leakage current and enable the manufacture of smaller sized transistors.

Along with the adoption of new dielectric materials and advanced structures, the need has arisen for measurement tools to characterize the dielectric properties and band structures of high-k materials early in the manufacturing process. In some examples, high throughput monitoring tools are required to monitor and control the deposition of high-k materials and the formation of various structures during wafer manufacture to ensure a high yield of finished wafers. Early detection of deposition problems is important because the complete manufacturing process of a semiconductor wafer is lengthy and expensive. For example, deposition of high-k materials often occurs at the beginning of a manufacturing process that takes over one month to complete.

Many existing process control and yield management tools produce measurement results only for the process step that they measure. This limits the value offered by many existing tools, since their measurements are not directly correlated with a final device performance that is weeks or hundreds process steps away from measurement. In addition, many existing process control and yield management tools do not offer insight into the sensitivity of various measured parameters to final device performance. For example, a composition measurement currently offered by a typical thin film metrology tool or a CD parameter measurement currently offered by a typical CD metrology tool, taken in isolation, does not provide direct insight into final device performance.

Measurements of the material composition of high-k dielectric layers have been used as indicators for process monitoring. For high-k materials such as SiHfON, it was found that differing percentages of nitrogen and hafnium, different deposition temperatures and deposition cycle times, different intermediate layers, etc., produce different dispersion values and different energy band structures. This affects chip performance at the end of the manufacturing process.

In some examples, an X-ray spectrometer has been utilized to accurately measure the material composition of high-k dielectric layers. However, X-ray spectroscopy suffers from high cost and low throughput, making it undesirable for use as a high throughput production monitoring tool.

In some other examples, dispersion properties of the high-k dielectric layer (e.g., refractive index, n, and extinction coefficient, k) have been used to calculate material composition based on empirical models. This approach has the advantage of lower cost and higher throughput relative to X-ray spectroscopic techniques. One such example is presented in U.S. patent application Ser. No. 13/524,053 assigned to KLA-Tencor Technologies, Corp.

Although the material composition of a high-k material layer is a strong indicator of deposition process parameters, it does not directly correlate with end of line electrical properties, such as leakage current, etc. For example, in the case of SiHfON, a shift of deposition rate and temperature may produce a film with differing structural defects or different band structure while material composition remains unchanged. The resulting structural defects or band structure may adversely increase leakage current, despite the fact that the material composition has not changed. Similarly, a process that produces a different material composition may also result in reduced structural defects and a more favorable band structure. In this case, monitoring based on material composition may result in a false negative result where fault is found based on material composition when in fact the material structure and properties results in reduced leakage current.

Accordingly, it would be advantageous to develop high throughput methods and/or systems for predicting final device performance based on an aggregation of measurements of structures and characterization of material layers early in the manufacturing process to identify whether resulting finished wafers will have satisfactory electrical properties.

SUMMARY

Methods and systems of process control and yield management for semiconductor device manufacturing based on predictions of final device performance are presented herein. Estimates of one or more final performance metrics of a semiconductor device are based on measurements of unfinished, multi-layer semiconductor wafers.

In one aspect, an estimated value of a device performance metric is based on at least one structural characteristic and at least one band structure characteristic of the unfinished, multi-layer wafer. Estimated device performance metric values are calculated based on one or more device performance models. Device performance models may take the form of physical mathematical models expressed in analytical or numerical forms. In some examples, device performance models are complete, full-chip simulation models, or models of sections or functional units of a chip. In some examples, component models formulated for building blocks of integrated circuits are employed. Some device models might involve tens or hundreds of free or constrained parameters. In some examples, the dimension of the device model is reduced by standard mathematical methods, such as correlation analysis, principle component analysis, etc. In some other examples, the device performance model is an empirical model constructed from simplified mathematical models. Such models may be formulated based on a correlation or statistical study, principal component analysis, or other data processing technique that links measured physical properties to measured electrical properties of a finished device.

In a further aspect, the device performance model is regressed and fine-tuned based on actual final electrical test data and measurement data available for a single device or multiple devices on multiple wafers. In this manner, model parameters are refined to improve the predictive capability of the device performance model.

In another further aspect, a statistical analysis of the device performance model is performed to provide insight into the expected performance of a particular semiconductor manufacturing process flow. For example, at any particular process step, each measured parameter and each nominal parameter can be characterized statistically, e.g., mean, range, standard deviation, etc. Based on these parameter values, the device performance model is used to derive the expected statistical values associated with one or more final device performance metrics, e.g., nominal value, average value, range, median, probabilities, etc.

In a further aspect, estimated values of one or more final device performance metrics are compared to specified final device performance values to determine whether the chip under process is expected to fail the final device performance test.

In yet another further aspect, an adjustment in one or more subsequent process steps is determined based on a difference between the estimated values of one or more final device performance metrics and the specified final device performance values. In some examples, the adjustment includes a change in a targeted nominal process value of a subsequent process step. The amount of adjustment is determined based on a sensitivity of a final device performance metric to the physical parameter subject to adjustment. These sensitivities may be calculated as derivatives of the device performance model with respect to the physical parameter subject to adjustment.

The foregoing is a summary and thus contains, by necessity, simplifications, generalizations, and omissions of detail. Consequently, those skilled in the art will appreciate that the summary is illustrative only and is not limiting in any way. Other aspects, inventive features, and advantages of the devices and/or processes described herein will become apparent in the non-limiting detailed description set forth herein.

DETAILED DESCRIPTION

Figure 1:
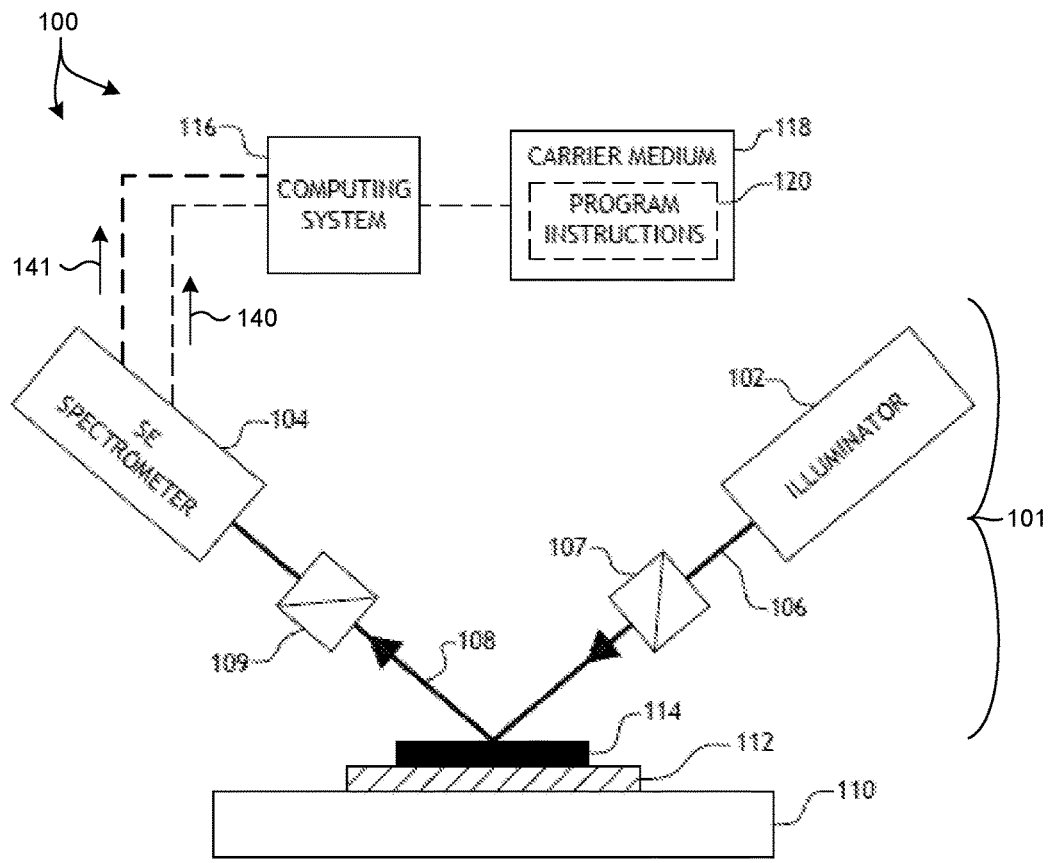
FIG. 1 is a simplified diagram illustrative of a semiconductor measurement system 100 configured to predict final device performance as described herein.

Reference will now be made in detail to background examples and some embodiments of the invention, examples of which are illustrated in the accompanying drawings.

Methods and systems of process control and yield management for semiconductor device manufacturing based on predictions of final device performance from measurements of unfinished, multi-layer semiconductor wafers are presented herein. Estimates of one or more performance metrics of a semiconductor device are made as if the semiconductor device were finished. The estimates are based on measurements of an unfinished, semiconductor wafer upon which the semiconductor device is to be constructed.

In one aspect, an estimated value of a device performance metric is based on at least one structural characteristic and at least one band structure characteristic of the unfinished, multi-layer wafer. The characteristics are measured either directly or indirectly. Estimated device performance metric values are calculated based on one or more device performance models.

Device performance models may take the form of physical mathematical models expressed in analytical or numerical forms. Device performance models can be complete, full-chip simulation models, or models of sections or functional units of a chip. Models capturing full functionality or a portion of the full functionality may be contemplated. In some embodiments, component models formulated for the building blocks of integrated circuits (e.g., p-MOS or n-MOS transistors, logic gates, etc.) are employed.

In some examples, the device performance model is formulated in electronic design automation (EDA) software, such as SPICE, etc. Some device models might involve tens or hundreds of free or constrained parameters. It is often desirable to reduce the model order to simplify subsequent analysis. In some examples, the dimension of the device model is reduced by standard mathematical methods, such as correlation analysis, principle component analysis, etc. In some examples, the device performance model is formulated based on a simplified device model that accounts for critical parameters with the greatest impact on final chip performance.

In some other examples, the device performance model is an empirical model constructed from simplified mathematical models such as a first order linear fit, or higher order linear fit. Such models may be formulated based on a correlation or statistical study, principal component analysis, or other data processing technique that links measured physical properties to measured electrical properties of a finished device.

In some examples, the device performance model includes only a few parameters, or even one parameter with the greatest impact. By way of non-limiting example, device performance model parameters may include energy band gap, energy band defect, or an empirical parameter derived from a combination of measured parameters.

In a further aspect, the device performance model is regressed and fine-tuned based on actual final electrical test data and measurement data available for a single device or multiple devices on multiple wafers. In this manner, model parameters are refined to improve the predictive capability of the device performance model.

In another further aspect, a statistical analysis of the device performance model is performed to provide insight into the expected performance of a particular semiconductor manufacturing process flow. For example, at any particular process step, each measured parameter and each nominal parameter can be characterized statistically, e.g., mean, range, standard deviation, etc. Based on these parameter values, the device performance model is used to derive the expected statistical values associated with one or more final device performance metrics, e.g., nominal value, average value, range, median, probabilities, etc.

At the beginning of the manufacturing process flow, a device performance model includes nominal (i.e., designed or expected) parameter values. Device performance is estimated during any particular process step by evaluating the device performance models at the process step using available measured values and nominal values of parameters that remain unmeasured or unconstructed. In this manner, the estimated values of final performance metrics are monitored at any step of the manufacturing process based on up to date measurement data.

In general, estimated values of final device performance metrics may be reevaluated at each process step. However, in most examples, a few critical processes in a semiconductor fabrication process flow are singled out for evaluation of final device performance metrics. In some of these examples, estimated values of final performance metrics are evaluated at a process step where a particular physical property is available for measurement and is a strong indicator of final device performance. For example, thin oxide deposition, or alternatively, high-K film deposition, is typically the critical step in the complementary metal oxide on silicon (CMOS) semiconductor fabrication process. At this step, band structure characteristics, such as band gap, band defects, etc., are strong indicators of the electrical performance of the final device.

At any process step, one or more dielectric parameters, structural parameters, energy band parameters, etc. are measured either directly or indirectly at the designated scribe line locations or on the chip itself. Certain characteristics that cannot be directly measured can be interpolated from measurements taken at different sites, or derived from other direct measurements. The measured parameters are used to update the parameters of the associated device model(s) for the designated measurement site or the wafer as a whole. The measurements may be performed by any suitable measurement technique. By way of non-limiting example, optical metrology tools, e-beam metrology tools, or x-ray metrology tools may be employed to perform such measurements.

In some examples, final device performance metrics include structural performance metrics such as equivalent oxide thickness. In some examples, these structural performance metrics may be employed to determine an expected electrical performance of the finished device. In some examples, the final device performance metrics are electrical performance metrics such as leakage current, threshold voltage, capacitance, breakdown voltage, mobility, etc.

The calculated device performance metric values are the expected performance values associated with the device to be finished if all subsequent process steps yield nominal results. As the manufacturing process proceeds, the device performance model can be updated at each monitoring step in the manufacturing process flow to include more measured values in place of nominal values. In this manner, the device performance model provides estimated values of final device performance metrics in real time at each fabrication step. Moreover, each process step is linked to the end-of-line chip performance metrics, avoiding the need to wait for weeks to obtain final test results after the chips are completely fabricated.

In a further aspect, estimated values of one or more final device performance metrics are compared to specified final device performance values to determine whether the chip under process is expected to fail the final device performance test. If the estimated values of one or more final device performance metrics falls outside of a specification window at any process step, it means that even if subsequent process steps all fall into their respective process window, the device will fail the final device performance test. In some examples, the device is removed from the processing line to avoid unnecessary cost to fully construct a part that will ultimately fail to meet specifications.

In another further aspect, an adjustment in one or more subsequent process steps is determined based on a difference between the estimated values of one or more final device performance metrics and the specified final device performance values. In some examples, the adjustment includes a change in a targeted nominal process value of a subsequent process step. For example, a film thickness that is too thin at a particular deposition step might be compensated by reducing an etching time at a later step. The amount of adjustment is determined based on a sensitivity of a final device performance metric to the physical parameter subject to adjustment. These sensitivities may be calculated as derivatives of the device performance model with respect to the physical parameter subject to adjustment.

If a physically realizable adjustment to a physical parameter is determined, the adjustment is communicated to the appropriate fabrication tool to perform the subsequent process step(s) with the adjusted target value. However, if no adjustment is determined, an indication of a suspect device is communicated, for example, to an operator. In response, the problem wafer may be removed from the production line for reprocessing or scrap. Alternatively, the wafer may be flagged for more stringent electrical test at the end of fabrication steps, etc.

FIG. 1 illustrates a system 100 for determining an estimate of a final electrical performance metric of an unfinished device of a multi-layer semiconductor wafer by way of non-limiting example. The estimate is based at least in part on a band structure characteristic and a structural characteristic measured by system 100, in accordance with one embodiment of the present invention. As shown in FIG. 1, the system 100 may be used to perform spectroscopic ellipsometry on one or more films 114 of a semiconductor wafer 112 disposed on a translation stage 110. In this aspect, the system 100 may include a spectroscopic ellipsometer equipped with an illuminator 102 and a spectrometer 104. The illuminator 102 of the system 100 is configured to generate and direct illumination of a selected wavelength range (e.g., 150-850 nm) to the thin film (e.g., HfSiON thin film) disposed on the surface of the semiconductor wafer 112. In turn, the spectrometer 104 is configured to receive illumination reflected from the surface of the semiconductor wafer 112. It is further noted that the light emerging from the illuminator 102 is polarized using polarizer 107 to produce a polarized illumination beam 106. The radiation reflected by the thin film 114 disposed on the wafer 112 is passed through an analyzer 109 and to the spectrometer 104. In this regard, the radiation received by the spectrometer 104 in the collection beam 108 is compared to the incident radiation of the illumination beam 106, allowing for spectral analysis of the thin film 114.

In a further embodiment, the system 100 may include one or more computing systems 116. The one or more computing systems 116 may be communicatively coupled to the spectrometer 104. In one aspect, the one or more computing systems 116 may be configured to receive a set of spectral measurements performed by the spectrometer 104 on one or more wafers. For example, as depicted in FIG. 1, spectral measurements 140 and 141 are communicated from spectrometer 104 to computing system 116. Spectral measurements 140 and 141 are measurements performed by a different sampling process (e.g., different measurement site, different spectral range, different step of the fabrication process, etc.). Upon receiving results of the one or more sampling process from the spectrometer, the one or more computing systems 116 may then calculate an optical dispersion metric. In this regard, the computing system 116 may extract the real component (n) and the imaginary component (k) of the complex index of refraction of the thin film across the selected spectral range (e.g., 150-850 nm) for the acquired spectrum from the spectrometer 104. Further, the computing system 116 may extract the n- and k-curves utilizing a regression process (e.g., ordinary least squares regression) applied to a selected dispersion model. In a preferred embodiment, the selected dispersion model may include a sum model with two Tauc Lorentz components (Sum-TL model). In other embodiments, the selected dispersion model may include a harmonic oscillator model.

Figure 3A:
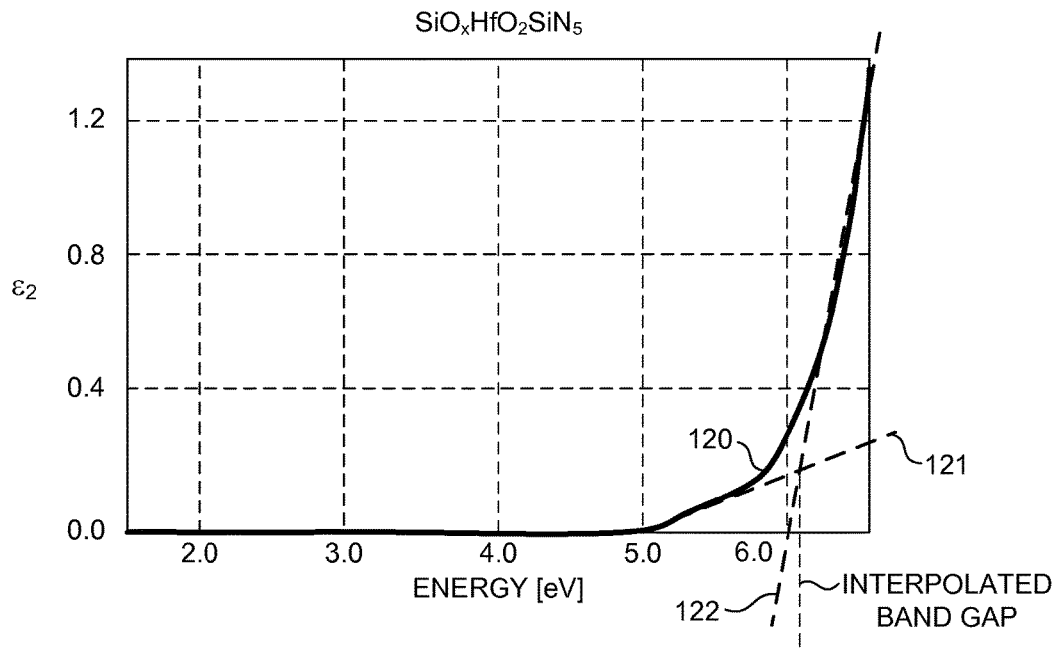
FIGS. 3A-3B are plots illustrative of optical dispersion curves associated with a thin film material layer and band structure characteristics derived from the curves.
Figure 3B:
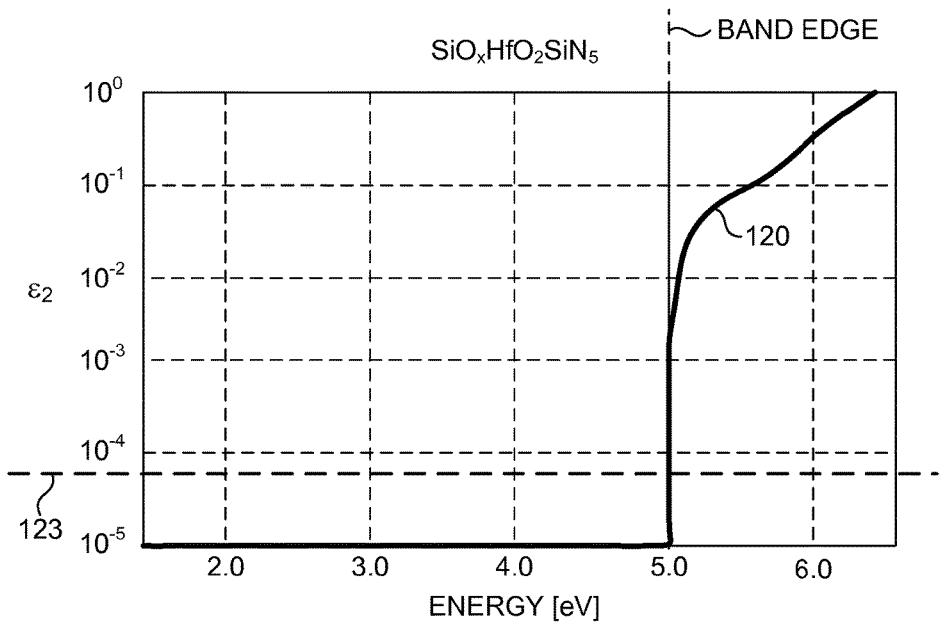
Figure 4:
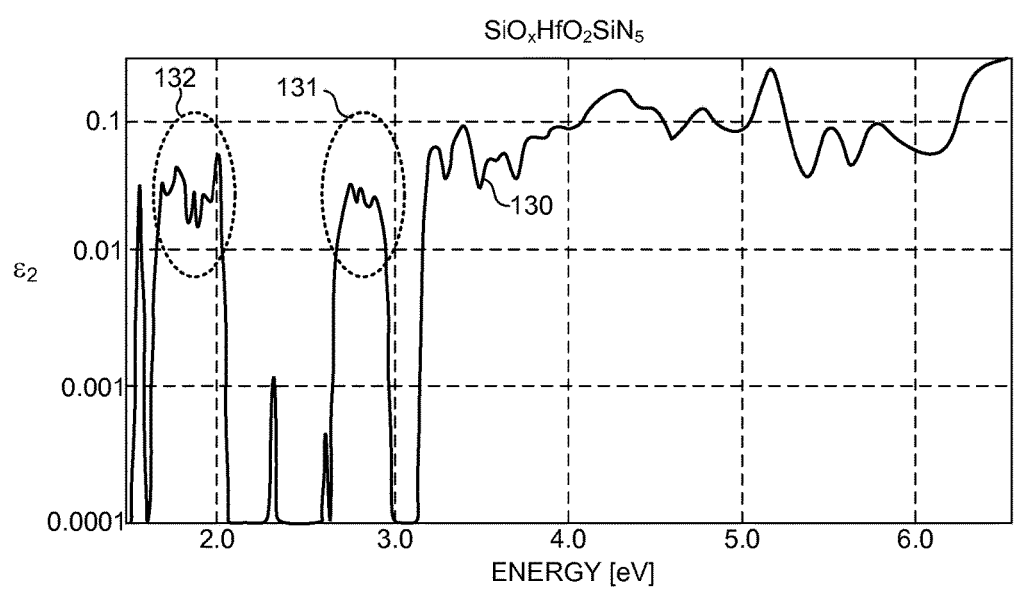
FIG. 4 is a plot illustrative of an optical dispersion curve associated with a thin film material layer and band structure defects identified from the curve.

In a further embodiment, the computing system 116 may determine a band structure characteristic indicative of an electrical performance of the film 114 based on the optical dispersion metric. For example, the computing system 116 may be configured to automatically identify trends within an optical dispersion curve (e.g., FIGS. 3A-3B and FIG. 4) that is representative of the value of the optical dispersion metric over the selected spectral range. For instance, the computing system 116 may identify energy band defects observable in an optical dispersion curve. In another example, the computing system 116 may identify the material band gap observable in an optical dispersion curve. In some examples, the computing system 116 may be configured to identify trends within an optical dispersion curve using the aid of user input. For instance, an optical dispersion curve may be presented to a user on a display (not shown), such as a liquid crystal display. The user may then identify trends in an optical dispersion curve by entering information into the computing system 116 using a user interface device (e.g., mouse, keyboard, trackpad, trackball, touch screen, or the like). In this regard, the user may select, or "tag," portions of the optical dispersion curves pertinent to analysis, with which the computing system may then, in turn, perform further or refined analysis. Applicant notes that specifics related to the analysis of optical dispersion curves, as shown in FIGS. 3A-3B and FIG. 4 will be discussed in greater detail further herein.

Figure 2:
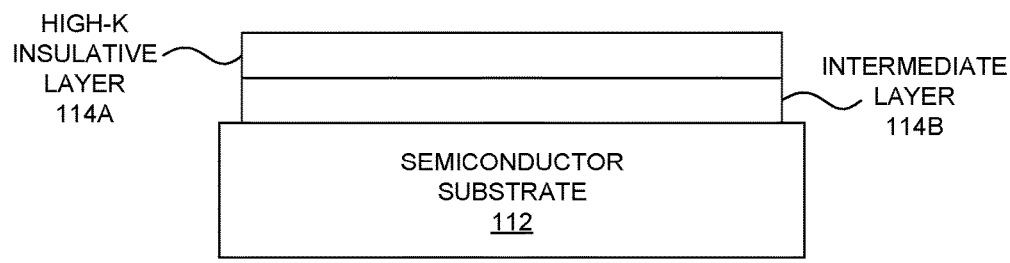
FIG. 2 is a simplified diagram illustrative of a semiconductor substrate 112 with attached thin film layers 114A and 114B that may be characterized by methods and systems as described herein.

As illustrated in FIG. 2, in some embodiments, an intermediate layer 114B is located between a semiconductor substrate 112 (e.g., silicon) and a high-k insulative layer 114A to promote adhesion between the high-k material and the semiconductor substrate. Typically, the intermediate layer 114B is very thin (e.g., ten Angstroms). In some examples, the high-k insulative layer 114A and the intermediate layer 114B are modeled together as one layer for purposes of analysis employing the methods and systems as described herein. In this example, the one or more computing systems 116 may determine a band structure characteristic indicative of an electrical performance of the film layer 114 including both the intermediate layer 114B and high-k insulative layer 114A based on an optical dispersion metric associated with the aggregate film layer 114. However, in some other examples, each layer may be modeled separately. In this example, the one or more computing systems 116 may determine a band structure characteristic indicative of an electrical performance of the high-k insulative layer 114A and a band structure characteristic indicative of an electrical performance of the intermediate layer 114B film layer based on optical dispersion metrics associated with each physically distinct layer, respectively.

It should be recognized that the various steps described throughout the present disclosure may be carried out by a single computer system 116 or, alternatively, a multiple computer system 116. Moreover, different subsystems of the system 100, such as the spectroscopic ellipsometer 101, may include a computer system suitable for carrying out at least a portion of the steps described above. Therefore, the above description should not be interpreted as a limitation on the present invention but merely an illustration. Further, the one or more computing systems 116 may be configured to perform any other step(s) of any of the method embodiments described herein.

In another embodiment, the computer system 116 may be communicatively coupled to the spectrometer 104 or the illuminator subsystem 102 of the ellipsometer 101 in any manner known in the art. For example, the one or more computing systems 116 may be coupled to a computing system of the spectrometer 104 of the ellipsometer 101 and a computing system of the illuminator subsystem 102. In another example, the spectrometer 104 and the illuminator 102 may be controlled by a single computer system. In this manner, the computer system 116 of the system 100 may be coupled to a single ellipsometer computer system.

The computer system 116 of the system 100 may be configured to receive and/or acquire data or information from the subsystems of the system (e.g., spectrometer 104, illuminator 102, and the like) by a transmission medium that may include wireline and/or wireless portions. In this manner, the transmission medium may serve as a data link between the computer system 116 and other subsystems of the system 100. Further, the computing system 116 may be configured to receive spectral results via a storage medium (i.e., memory). For instance, the spectral results obtained using a spectrometer of an ellipsometer may be stored in a permanent or semi-permanent memory device. In this regard, the measurement results may be imported from an external system. Moreover, the computer system 116 may send data to external systems via a transmission medium.

The computer system 116 of the system 100 may be configured to receive and/or acquire data or information from other systems (e.g., inspection results from an inspection system or metrology results from a metrology system) by a transmission medium that may include wireline and/or wireless portions. In this manner, the transmission medium may serve as a data link between the computer system 116 and other subsystems of the system 100. Moreover, the computer system 116 may send data to external systems via a transmission medium.

Figure 8:
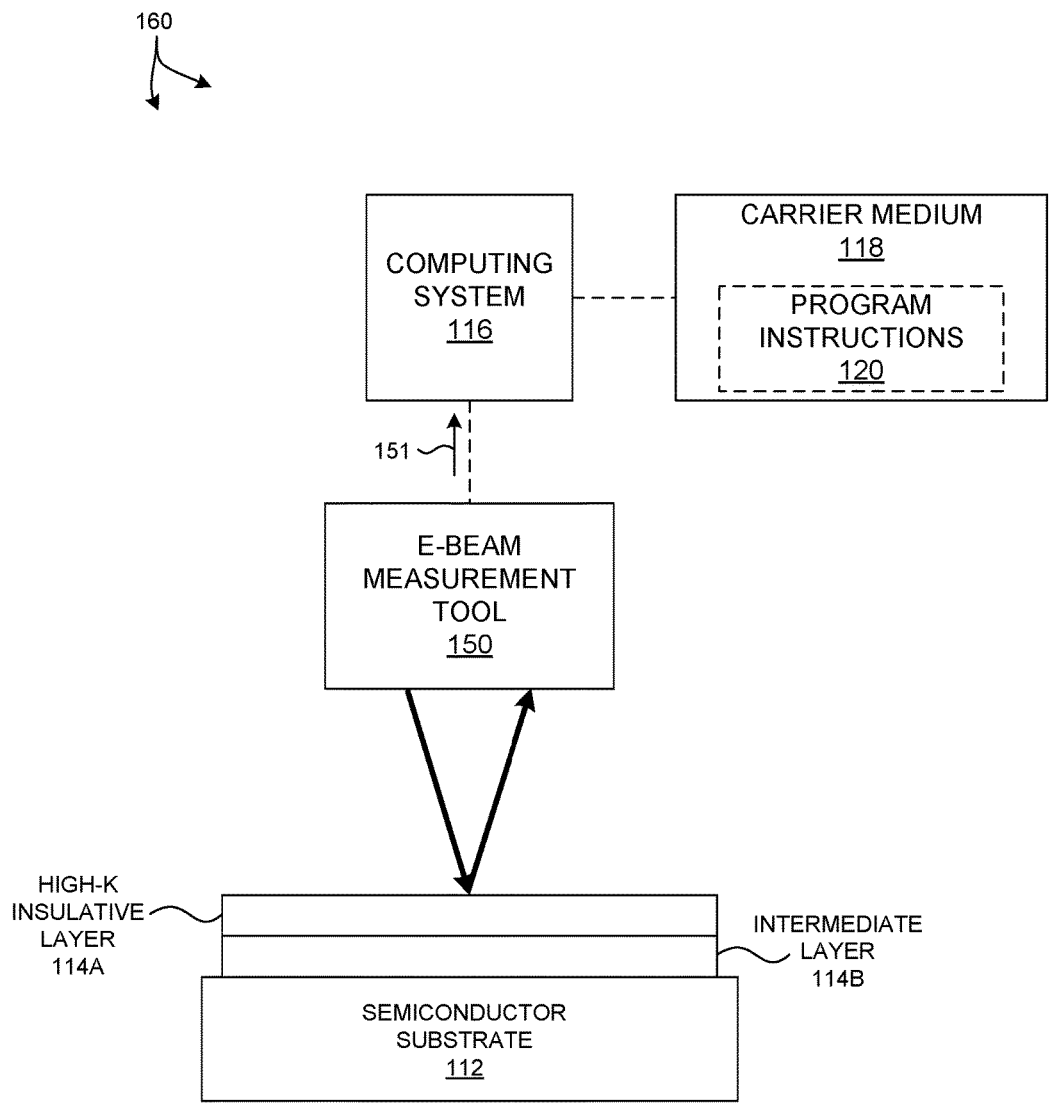
FIG. 8 is a simplified diagram illustrative of a semiconductor measurement system 160 configured to predict final device performance as described herein.

In general, measurement data from all types of metrology tools, such as optical measurement tools, e-beam measurement tools, x-ray measurement tools, etc., may be combined to predict final device performance from measurements of unfinished wafers as described herein. In some embodiments, a metrology tool incorporates multiple illumination sources having spanning different wavelength ranges, e.g., soft x-ray, ultraviolet (DUV, EUV, VUV, etc.), visible, infrared, far IR, etc. In some embodiments, a metrology tool incorporates multiple measurement methods, such as single wavelength or broadband ellipsometers or reflectometers, different angular spaces. In some embodiments, a metrology tool incorporates multiple measurement techniques, such as e-beam based metrology, x-ray based metrology, etc. In general, measurement data, regardless of source, may be aggregated to enhance the precision and stability of measurements of band structure and structural characteristics of unfinished semiconductor wafers for purposes of predicting the performance of finished wafers. For example, FIG. 8 depicts computing system 116 receiving measurement results 151 from an e-beam measurement system 150 that performs measurements of the same unfinished device of the multi-layer semiconductor wafer as measured by ellipsometer 101.

In general, measurement data employed to predict the performance of finished wafers as described herein, is received by one or more computing systems. The one or more computing systems may be integrated with a particular measurement tool as depicted in FIG. 1, or the one or more computing systems may be located remotely from any particular measurement tool (e.g., a remotely located centralized server or distributed server system). In this manner, the collection and analysis of measurement data as described herein may be undertaken by one or more computing systems, either collocated, or remotely located from any particular measurement tool.

Moreover, measurement data for designated wafers undergoing a manufacturing process flow is identified and stored for analysis as described herein. For example, measurement data may be tagged to identify the particular wafer (waferID), measurement site (siteID), process step (processed), time stamps, etc. Tagged measurement data may be stored in a centralized location, such as a memory of a particular measurement tool (e.g., carrier medium 118 depicted in FIG. 1) or on a centralized or distributed server system. The measurement data can then be accessed by various tools for monitoring related purposes.

The computing system 116 may include, but is not limited to, a personal computer system, mainframe computer system, workstation, image computer, parallel processor, or any other device known in the art. In general, the term "computing system" may be broadly defined to encompass any device having one or more processors, which execute instructions from a memory medium.

Program instructions 120 implementing methods such as those described herein may be transmitted over or stored on carrier medium 118. The carrier medium may be a transmission medium such as a wire, cable, or wireless transmission link. The carrier medium may also include a computer-readable medium such as a read-only memory, a random access memory, a magnetic or optical disk, or a magnetic tape.

The embodiments of the system 100 illustrated in FIG. 1 may be further configured as described herein. In addition, the system 100 may be configured to perform any other step(s) of any of the method embodiment(s) described herein.

Band structure characteristics (e.g., band gap, band edge, energy band defects, interface defects, band broadening, etc.) and structural characteristics (e.g., thickness, CD, etc.) of material structures of unfinished wafers are suitable indicators of the final device performance of finished wafers. In one example, band structure characteristics are major contributors to unintended leakage current through high-k material layers of finished wafers. Measured band structure characteristics and measured structural characteristics are fed into the device performance model to predict final device performance metrics of finished wafers at an early point in the manufacturing process.

Figure 5:
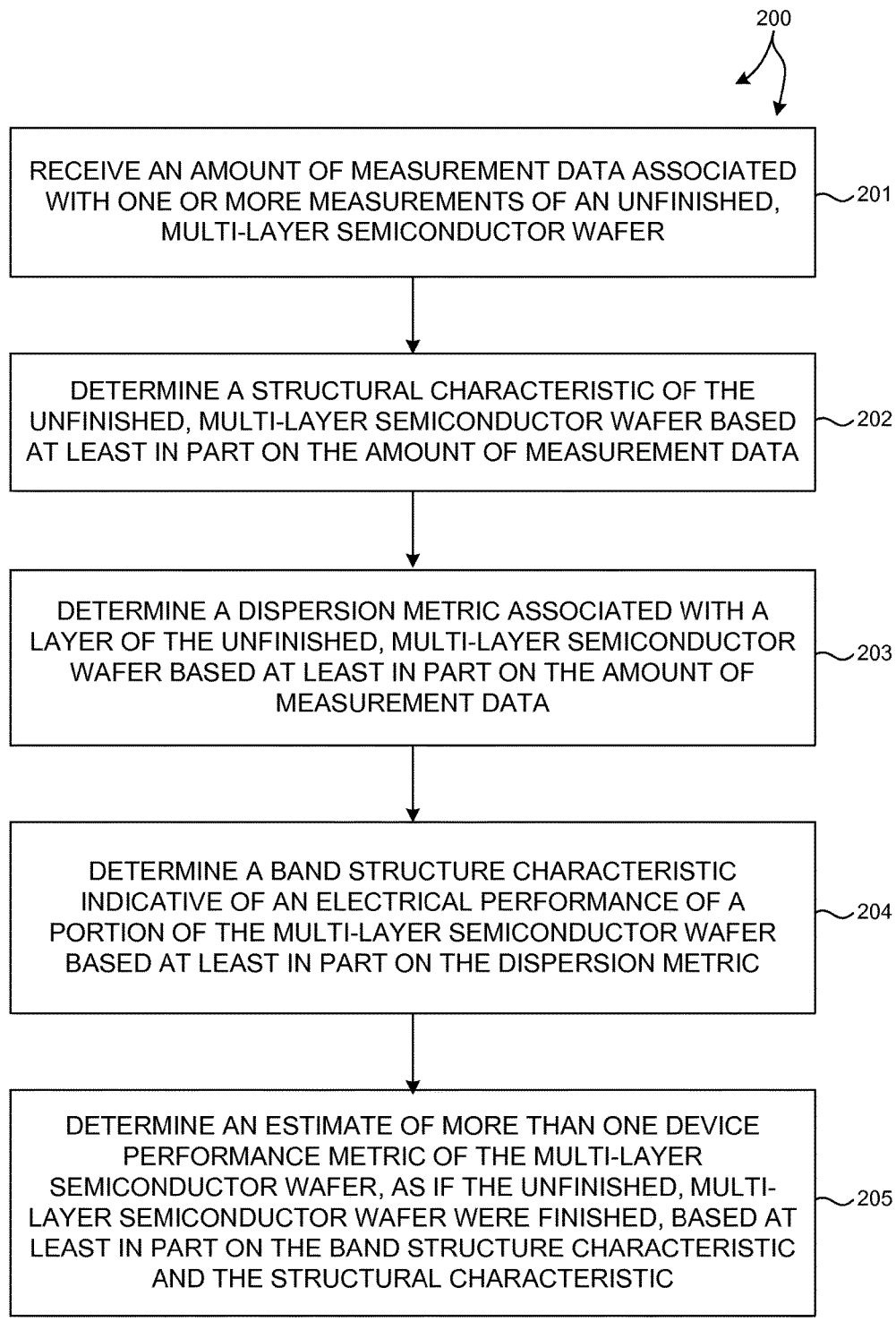
FIG. 5 is a flowchart illustrative of a method 200 of predicting final device performance from measurement data collected from unfinished wafers.

FIG. 5 illustrates a process flow 200 suitable for implementation by the system 100 of the present invention. In one aspect, it is recognized that data processing steps of the process flow 200 may be carried out via a pre-programmed algorithm executed by one or more processors of computing system 116. While the following description is presented in the context of system 100, it is recognized herein that the particular structural aspects of system 100 do not represent limitations and should be interpreted as illustrative only.

In block 201, an amount of measurement data associated with one or more measurements of an unfinished, multi-layer semiconductor wafer are received, for example, by computing system 116. In some examples, a spectral response of an unfinished, multi-layer semiconductor wafer across a broad spectral range is received after a high-k thin film is deposited on the wafer. For example, spectra may be received from an ellipsometer 101. In another example, spectra may be received from a reflectometer (not shown). The spectral data may be acquired from each of the thin films 114 deposited on the wafer 112 utilizing the spectroscopic ellipsometer 101. For instance, the ellipsometer 101 may include an illuminator 102 and a spectrometer 104, as discussed previously herein. The spectrometer 104 may transmit results associated with a spectroscopic measurement of the thin films of the wafer to one or more computing systems 116 for analysis. In another example, the spectra for multiple thin films 114 may be acquired by importing previously obtained spectral data. In this regard, there is no requirement that the measurement data acquisition and the subsequent analysis of the measurement data need be contemporaneous or performed in spatial proximity. For instance, measurement data may be stored in memory for analysis at a later time. In another instance, measurement results may be obtained and transmitted to a computing system located at a remote location for further analysis.

In block 202, a structural characteristic of the unfinished, multi-layer semiconductor wafer is determined based at least in part on the amount of measurement data. For example, computing system 116 may compute a thickness of high-K insulative layer 114A, intermediate layer 114B, or the combined thickness of both layers based on the received measurement data.

In block 203, an optical dispersion metric associated with a layer of the semiconductor wafer is determined based on the measurement data. Many useful optical dispersion metrics may be contemplated. For example, any of the real (n) and imaginary (k) components of the complex index of refraction may be determined based on the spectral data. In another example, any of the real ($\varepsilon_1$) and imaginary ($\varepsilon_2$) components of the complex dielectric constant may be determined based on the spectral data. In other examples, any of the square root of $\varepsilon_2$, absorption constant $\alpha=4\pi k/\lambda$, conductivity ($\sigma$), skin depth ($\delta$), and attenuation constant $(\sigma/2)*\mathrm{sqrt}(\mu/\varepsilon)$ may be determined based on the spectral data. In other examples, any combination of the aforementioned optical dispersion metrics may be determined based on the spectral data. The aforementioned optical dispersion metrics are provided by way of non-limiting example. Other optical dispersion metrics or combinations of metrics may be contemplated.

In some examples, the spectral response data is processed to determine film thickness and dispersion metrics (e.g., n and k) from an analytical dispersion model (e.g., Lorentzian models). In some other examples, spectral response data is processed to determine film thickness and dispersion metrics (e.g., n and k) from an empirical dispersion model where the dispersion metric is calculated numerically.

In one example, Off-Line Spectral Analysis (OLSA) software available from KLA-Tencor Corporation (Milpitas, Calif.) is used to numerically calculate any of k, $\varepsilon_2$, $\sigma$ and other user-defined metrics without exact knowledge of the dispersion property of a material. In a preferred example, $\varepsilon_2$, is calculated using OLSA based on spectral data taken by an ellipsometer from a wafer 112 including a thin film layer 114A of $SiO_xHfO_2SiN_5$ material. The locus of values 120 of $\varepsilon_2$ is illustrative of dispersion metric, $\varepsilon_2$, over a measured spectral range. FIG. 3B illustrates the same locus of values 120 plotted in logarithmic format.

In some examples, the optical dispersion metric may be generated by extracting the real component (n) and the imaginary component (k) of the complex index of refraction across the selected spectral range for the acquired spectrum utilizing a regression process applied to a selected dispersion model. In this regard, a regression method may be applied to the measured spectral data using a selected dispersion model. In one embodiment, a sum model with two Tauc-Lorentz components may be utilized to generate the n- and k-dispersion curves for each of the thin films of the wafers. In another embodiment, a single component Tauc-Lorentz may be utilized to generate the n- and k-dispersion curves for each of the thin films of the wafers. In another embodiment, a Cody-Lorentz model may be utilized to generate the n- and k-dispersion curves for each of the thin films of the wafers. In yet another embodiment, a harmonic oscillator model may be utilized to generate the n- and k-dispersion curves for each of the thin films of the wafers.

In block 204, a band structure characteristic indicative of an electrical performance of a portion of the multi-layer semiconductor wafer is determined based at least in part on the optical dispersion metric. In some examples, the band structure characteristic is determined across a subset of the available spectral range. Typically, limiting the spectral range for identification of a band structure characteristic is preferred because dispersion model results are generally more accurate over smaller spectral ranges. Thus, it may be advantageous to identify dispersion metric values from spectral data over a broad range initially to identify areas where more detailed analysis should be focused (e.g., near the band gap of the material). Based on this knowledge, the dispersion models may be recalculated based on a smaller range of spectral data. In some examples, identification of band structure characteristics is based on spectral data within a range of 0.5 to 10 electron volts. In some examples, identification of band structure characteristics is based on spectral data within a range of 2 to 6 electron volts Based on the energy region of interest, a band structure characteristic is determined.

In some examples, the band structure characteristic is determined directly from dispersion models applied to the particular film layer. For example, an analytical model, empirical model, or a combination of both analytical and empirical models includes a model of dispersion with a band structure characteristic (e.g., band gap) as a parameter. In this manner the band structure characteristic is determined directly through regression of the dispersion model (i.e., the model solution itself determines the band structure characteristic).

In some examples, the band structure characteristic is determined by analysis of the values of an optical dispersion metric (e.g., k, ε2 or other parameters that describe the absorption or extinction of electromagnetic energy by the high-k material) over a spectral range.

In one example, a band structure characteristic is a band edge value determined from an optical dispersion metric. As illustrated in FIG. 3B, a band edge value is defined when $\varepsilon_2$ exceeds a threshold value 123. In the illustrated example, a band edge value of the measured film is five electron volts.

In another example, a band structure characteristic is an interpolated band gap value determined by curve fitting and interpolation of an optical dispersion metric. For example, as illustrated in FIG. 3A, an interpolated band gap is determined based on curve fitting and interpolation of $\varepsilon_2$. In general, the amorphous structure of a high-k material, layer interfaces, and misaligned energy bands contribute to the broadening of the absorption edges at lower energy levels. Curve fitting methods are used to determine an interpolated band gap that significantly reduces the impact of broadening effects in the determination of band gap. For example, as illustrated in FIG. 3A, line 121 is representative of a linear fit to values of $\varepsilon_2$ between five electron volts and 5.5 electron volts. Line 122 is representative of a linear fit to values of $\varepsilon_2$ between 6.2 electron volts and 6.7 electron volts. Their intersection at approximately six electron volts is the interpolated band gap value. Although, as illustrated, lines 121 and 122 are linear fits to values of $\varepsilon_2$ over different spectral regions, other fitting methods may be employed. For example, higher order polynomial functions, exponential functions, or other mathematical functions may be used to fit optical dispersion values over different spectral regions to obtain an estimate of band gap of the measured film layer.

As illustrated in FIGS. 3A-3B, the interpolated band gap that discounts broadening effects and the band edge value that includes broadening effects are different values. The difference between the interpolated band gap and the band edge can be used as a band structure characteristic indicative of the magnitude of broadening effects present in the measured film. In this manner, process improvements can be separately judged based on their impact on broadening effects and on band gap absent broadening effects.

In another example, a band structure characteristic is a defect identified by analysis of an optical dispersion metric.

FIG. 4 illustrates the imaginary portion, $\varepsilon_2$, of the complex dielectric constant, k, of an exemplary high-k material, $SiO_xHfO_2SiN_5$, obtained from ellipsometry data using Off-Line Spectral Analysis (OLSA) software available from KLA-Tencor Corporation (Milpitas, Calif.). Optical measurements using an ellipsometer or a reflectometer are effective for measuring energy band structures in the 1.3-3 eV range, as illustrated in FIG. 4. In contrast, X-ray photoelectron spectroscopy (XPS) measurements are limited to measurement of band gap at energy levels greater than five electron volts.

Dispersion curve 130 illustrates defect modes and absorption lines associated with the $SiO_xHfO_2SiN_5$ film. By way of example, defects can be identified based on the curve 121 in a number of different ways.

In some examples, a defect is identified if the magnitude of the dispersion metric exceeds a threshold value at any point within a selected spectral range. In some examples, the selected spectral range is below the band gap of measured film. For example, as illustrated in FIG. 4, there are three instances when the magnitude of $\varepsilon_2$ exceeds a value of 0.01 within the spectral range of 1.3-3 electron volts (well below the band gap of the $SiO_xHfO_2SiN_5$ film). These include defects 131 and 132 identified in FIG. 4.

In some examples, a defect is identified if the full width, half maximum (FWHM) value of the dispersion metric exceeds a threshold value at any point within a selected spectral range. In some examples, the spectral location of a peak or defect region is used to identify a defect. For example, it may be known that a particular defect always manifests itself as a peak at a particular spectral energy level. In this case, a peak at that energy level may be identified with that particular defect. In some examples, the area under the peak or defect region is used to identify a defect. In some examples, the number of absorption peaks within a selected spectral range is used to identify a defect.

The aforementioned examples are provided for illustration purposes and do not limit the type of band structure characteristics that may be contemplated. Many other band structure characteristics that correlate with the electrical properties, and thus act as effective indicators of the performance of a finished wafer, may be contemplated.

Figure 6:
FIG. 6 is a table illustrative of values for film thickness and two band structure characteristics at different locations of an unfinished semiconductor wafer determined using methods and systems as described herein.

In block 205, an estimate of more than one device performance metric of the multi-layer semiconductor wafer is determined based at least in part on the band structure characteristic and the structural characteristic. As illustrated in FIG. 6, table 300 includes values for film thickness and two band structure characteristics (defect peak value and defect width) at different locations of an unfinished semiconductor wafer determined using the methods and systems discussed herein. As illustrated, the film thickness, defect peak value, and defect width are identified in five different locations of the wafer. In this example, an estimate of a performance metric (e.g., current density) of the finished wafer at each location is determined based on the linear model of equation (1). In this example, the electrical performance is a function of film thickness (T), defect peak ($D_{peak}$) and defect width ($D_{width}$).

$$\text{Perf}_{electrical} = 8.0351 - 1.2729*T + 36.9009*D_{peak} - 10.25 \\ 42*D_{width} \quad (1)$$

Figure 7:
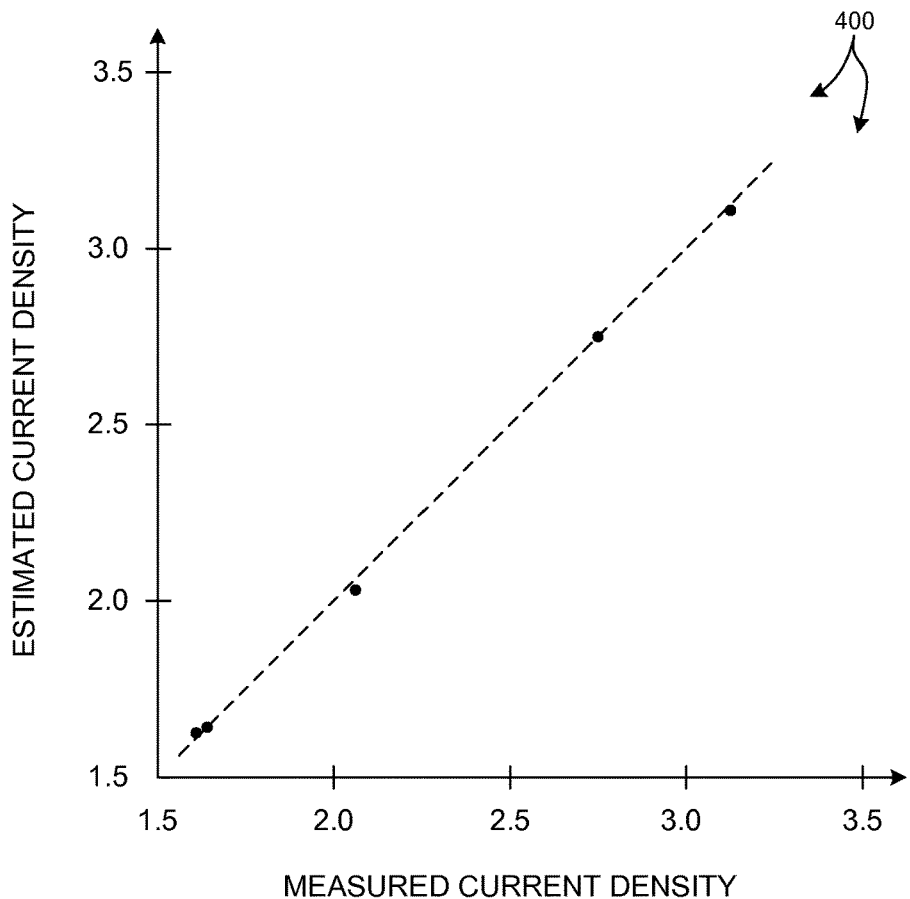
FIG. 7 is a plot illustrative of comparing the estimated current density and the measured current density of the finished wafer at different locations.

FIG. 7 illustrates a plot 400 comparing the current density estimated using the model of equation (1) and the measured current density of the finished wafer at these locations. In this example, the actual electrical performance of the finished wafer is estimated by the linear model of equation (1) with a coefficient of determination (R2) of 0.99.

The model of equation (1) is provided by way of non-limiting example. Many other models (e.g., nonlinear, exponential, etc.) may be identified to accurately relate band structure and structural characteristics identified early in the manufacturing process to electrical performance of finished wafers. In some examples, model parameters are resolved based on identified band structure characteristics and the corresponding measured electrical performance of finished wafers. Once the model parameters have been calculated, the model is used to estimate electrical performance of finished wafers based on band structure and structural characteristics identified early in the manufacturing process. Models incorporating any combination of band structure characteristic and structural characteristics may be contemplated. Current density is presented herein as an exemplary electrical performance metric, however, any other electrical performance metric useful to characterize finished wafers may be contemplated.

By way of non-limiting example, leakage current, capacitance, equivalent oxide thickness (EOT), threshold voltage, breakdown voltage, mobility, etc, are device performance metrics that may be determined in accordance with the methods and systems described herein. In one example, threshold voltage, may be calculated as illustrated in equation (2).

$$V_T = f(SiO_{thickness}, \text{Bandgap}) \quad (2)$$

In another example, equivalent oxide thickness (EOT) may be calculated as illustrated in equation (3).

$$EOT = g(SiO_{thickness}, HfO_{thickness}, \text{Bandgap}) \quad (3)$$

In one further aspect, separate determinations of optical dispersion metrics and band structure characteristics associated with different layers of a wafer can be made based on the same spectral response data. For example, a wafer under measurement may include a semiconductor substrate 112, an intermediate layer 114B, a high-k insulative layer 114A, and an additional film layer (not shown). The spectral response data received from spectrometer 104 includes contributions from all of these layers. A stack layer model that captures the contributions of each of these layers can be used to separately determine optical dispersion metrics and band structure characteristics associated with each different physical layer or group of physical layers under analysis.

In another further aspect, the stack model includes a model of the intrinsic absorption peaks of the semiconductor substrate 112 (e.g., silicon). In one example, the intrinsic absorption peaks are accounted for in the spectral measurement of the high-k film. In this manner, the absorption peaks of the semiconductor substrate may be effectively removed from the spectral response of the high-k film. By isolating the spectral response of the high-k film from the semiconductor substrate, a more accurate determination of defects and band structure characteristics associated with the high-k film layer is achieved.

In another further aspect, band structure characteristics (e.g., band gap and defects) are used to grade wafers and microchips early in the production process based on the quality of the gate insulator. This may avoid the need to grade wafers and microchips at the end of the production process using expensive and time consuming electrical test equipment.

The methods and systems described herein are generally applicable to the characterization of any semiconductor device and prediction of performance of the finished device early in the manufacturing process flow. This includes novel nano-materials and structures that may be adopted by the semiconductor industry in future technology nodes. For example, the fabrication of nanowire, single electron transistors, etc., can all be managed in accordance with the methods and systems described herein.

In one or more exemplary embodiments, the functions described may be implemented in hardware, software, firmware, or any combination thereof. If implemented in software, the functions may be stored on or transmitted over as one or more instructions or code on a computer-readable medium. Computer-readable media includes both computer storage media and communication media including any medium that facilitates transfer of a computer program from one place to another. A storage media may be any available media that can be accessed by a general purpose or special purpose computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code means in the form of instructions or data structures and that can be accessed by a general-purpose or special-purpose computer, or a general-purpose or special-purpose processor. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, optical disc, digital versatile disc (DVD), floppy disk and blu-ray disc where disks usually reproduce data magnetically, while discs reproduce data optically with lasers. Combinations of the above should also be included within the scope of computer-readable media.

As used herein, the term "wafer" generally refers to substrates formed of a semiconductor or non-semiconductor material. Examples of such a semiconductor or non-semiconductor material include, but are not limited to, monocrystalline silicon, gallium arsenide, and indium phosphide. Such substrates may be commonly found and/or processed in semiconductor fabrication facilities.

One or more layers may be formed upon a wafer. For example, such layers may include, but are not limited to, a resist, a dielectric material, a conductive material, and a semiconductive material. Many different types of such layers are known in the art, and the term wafer as used herein is intended to encompass a wafer on which all types of such layers may be formed.

One or more layers formed on a wafer may be patterned or unpatterned. For example, a wafer may include a plurality of dies, each having repeatable patterned features. Formation and processing of such layers of material may ultimately result in completed devices. Many different types of devices may be formed on a wafer, and the term wafer as used herein is intended to encompass a wafer on which any type of device known in the art is being fabricated.

A typical semiconductor process includes wafer processing by lot. As used herein a "lot" is a group of wafers (e.g., group of 25 wafers) which are processed together. Each wafer in the lot is comprised of many exposure fields from the lithography processing tools (e.g. steppers, scanners, etc.). Within each field may exist multiple die. A die is the functional unit which eventually becomes a single chip. One or more layers formed on a wafer may be patterned or unpatterned. For example, a wafer may include a plurality of dies, each having repeatable patterned features. Formation and processing of such layers of material may ultimately result in completed devices. Many different types of devices may be formed on a wafer, and the term wafer as used herein is intended to encompass a wafer on which any type of device known in the art is being fabricated.

Although embodiments are described herein with respect to wafers, it is to be understood that the embodiments may be used for characterizing thin films of another specimen such as a reticle, which may also be commonly referred to as a mask or a photomask. Many different types of reticles are known in the art, and the terms "reticle," "mask," and "photomask" as used herein are intended to encompass all types of reticles known in the art.

The embodiments described herein generally relate to methods and systems for predicting the final performance of semiconductor devices based on measurements performed during the manufacturing process. For example, one embodiment relates to a computer-implemented method for determining band structure characteristics of multi-layer thin films based on optical dispersion metrics derived from spectroscopic ellipsometer data. However, the methods described herein are not limited in the types of inspection systems from which optical dispersion metrics may be derived. For example, in one embodiment, the inspection system includes a rotating compensator type ellipsometer or a reflectometer for thin film inspection of the wafer. Many other measurement technologies may be contemplated within the scope of this patent document including optical, e-beam, and x-ray based measurement techniques. In addition, the analysis of high-k dielectric layers are described herein in some detail. However, the methods and systems described herein are not limited in the types of materials that may be subject to measurement and analysis in accordance with the techniques described herein. For example, analysis of work function layers (AlO, LaO), SiGe, III-V, ONO, ZAZ, ON, NO, BEOL dielectrics, and others may be contemplated within the scope of this patent document.

In addition, the inspection system may be configured for inspection of patterned wafers and/or unpatterned wafers. The inspection system may be configured as a LED inspection tool, edge inspection tool, backside inspection tool, macro-inspection tool, or multi-mode inspection tool (involving data from one or more platforms simultaneously), and any other metrology or inspection tool that benefits from the determination of band structure characteristics of multi-layer thin films based on optical dispersion metrics at high throughput.

Although certain specific embodiments are described above for instructional purposes, the teachings of this patent document have general applicability and are not limited to the specific embodiments described above. Accordingly, various modifications, adaptations, and combinations of various features of the described embodiments can be practiced without departing from the scope of the invention as set forth in the claims.

What is claimed is:

1. A method comprising:
illuminating a measurement site of an unfinished, multi-layer semiconductor wafer with illumination light;
polarizing the illumination light before incidence on the semiconductor wafer;
analyzing light collected from the measurement site of the semiconductor wafer in response to the polarized illumination light provided to the semiconductor wafer;
detecting the analyzed light with a spectrometer;
generating a measured spectral response of the measurement site of the unfinished, multi-layer semiconductor wafer from the analyzed light detected by the spectrometer, the measured spectral response comprising measurement data;
determining a structural characteristic of the unfinished, multi-layer semiconductor wafer based at least in part on the measurement data;
determining a dispersion metric associated with a layer of the unfinished, multi-layer semiconductor wafer based at least in part on the measurement data;
determining a band structure characteristic indicative of an electrical performance of a portion of the multi-layer semiconductor wafer based at least in part on the dispersion metric;
determining an estimate of one or more device performance metrics of the multi-layer semiconductor wafer, as if the unfinished, multi-layer semiconductor wafer were finished, based at least in part on the band structure characteristic and the structural characteristic;
determining an adjustment in one or more subsequent process steps based on a difference between the estimated values of the one or more device performance metrics and one or more corresponding specified final device performance values, wherein the adjustment includes a change in a targeted nominal process value of a subsequent process step; and
communicating an indication of the adjustment to a fabrication tool to perform the subsequent process step in accordance with the adjustment.

2. The method of claim 1, wherein the measurement data includes measurement data associated with a measurement of the unfinished, multi-layer semiconductor wafer at a first process step and measurement data associated with a measurement of the unfinished, multi-layer semiconductor wafer at a second process step.

3. The method of claim 1, wherein the measurement data includes measurement data associated with a measurement of the unfinished, multi-layer semiconductor wafer by an optical measurement system and measurement data associated with a measurement of the unfinished, multi-layer semiconductor wafer by a measurement system different from the optical measurement system.

4. The method of claim 1, wherein the measurement data includes measurement data associated with a measurement of the unfinished, multi-layer semiconductor wafer performed by one or more of any of an optically based measurement tool, an e-beam based measurement tool, and an x-ray based measurement tool.

5. The method of claim 1, wherein the measurement data includes measurement data associated with measurements over a first spectral range, and wherein the band structure characteristic indicative of the electrical performance of the unfinished, multi-layer semiconductor wafer is based at least in part on the dispersion metric of the unfinished, multi-layer semiconductor wafer across a second spectral range within the first spectral range.

6. The method of claim 1, further comprising:
determining whether a device under process is expected to fail a final device performance test based on comparing the estimate of a device performance metric value and a specified final device performance value.

7. The method of claim 1, wherein the band structure characteristic is an interpolated band gap of an electrically insulative layer disposed above a semiconductor substrate and the determining of the interpolated band gap involves curve fining and interpolation of the optical dispersion metric.

8. The method of claim 1, wherein the band structure characteristic is a band edge of an electrically insulative layer disposed above a semiconductor substrate and the determining of the band edge involves determining that the optical dispersion metric exceeds a threshold value.

9. The method of claim 1, wherein the band structure characteristic is a band broadening associated with an electrically insulative layer disposed above a semiconductor substrate and the determining of the band broadening involves determining an interpolated band gap and a band edge of the first layer and determining a difference between the band edge and the interpolated band gap.

10. The method of claim 1, wherein the band structure characteristic is a defect and the determining of the defect involves determining whether the optical dispersion metric exceeds a threshold value over a spectral range below a band gap of an electrically insulative layer disposed above a semiconductor substrate.

11. A measurement system comprising:
an illuminator that provides illumination light to a measurement site of an unfinished, multi-layer semiconductor wafer;
a spectrometer that detects light from the measurement site in response to the illumination light and generates a measured spectral response of the measurement site, the measured spectral response comprising measurement data; and
a non-transitory, computer-readable medium storing instructions that, when executed by one or more processors, cause the one or more processors to:
determine a structural characteristic of the unfinished, multi-layer semiconductor wafer based at least in part on the measurement data;
determine a dispersion metric associated with a layer of the unfinished, multi-layer semiconductor wafer based at least in part on the measurement data;
determine a band structure characteristic indicative of an electrical performance of a portion of the multi-layer semiconductor wafer based at least in part on the dispersion metric;
determine an estimate of one or more device performance metrics of the multi-layer semiconductor wafer, as if the unfinished, multi-layer semiconductor wafer were finished, based at least in part on the band structure characteristic and the structural characteristic;
determine an adjustment in one or more subsequent process steps based on a difference between the estimated values of the one or more device performance metrics and one or more corresponding specified final device performance values, wherein the adjustment includes a change in a targeted nominal process value of a subsequent process step; and communicate an indication of the adjustment to a fabrication tool to perform the subsequent process step in accordance with the adjustment.

12. The measurement system of claim 11, wherein the measurement data includes measurement data associated with a measurement of the unfinished, multi-layer semiconductor wafer at a first process step and measurement data associated with a measurement of the unfinished, multi-layer semiconductor wafer at a second process step.

13. The measurement system of claim 11, wherein the measurement data includes measurement data associated with a measurement of the unfinished, multi-layer semiconductor wafer by an optical measurement system and measurement data associated with a measurement of the unfinished, multi-layer semiconductor wafer by a measurement system different from the optical measurement system.

14. The measurement system of claim 11, wherein the measurement data includes measurement data associated with a measurement of the unfinished, multi-layer semiconductor wafer performed by one or more of any of an optically based measurement tool, an e-beam based measurement tool, and an x-ray based measurement tool.

15. The measurement system of claim 11, wherein the measurement data includes measurement data associated with measurements over a first spectral range, and wherein the band structure characteristic indicative of the electrical performance of the unfinished, multi-layer semiconductor wafer is based at least in part on the dispersion metric of the unfinished, multi-layer semiconductor wafer across a second spectral range within the first spectral range.

16. The measurement system of claim 11, the non-transitory, computer-readable medium further storing instructions that, when executed by the one or more processors, cause the one or more processors to:
determine whether a device under process is expected to fail a final device performance test based on comparing the estimate of a device performance metric value and a specified final device performance value.

17. The measurement system of claim 11, the non-transitory, computer-readable medium further storing instructions that, when executed by the one or more processors, cause the one or more processors to:
determine an adjustment in one or more subsequent process steps based on a difference between the estimate of a device performance metric value and a specified final device performance value.

18. A system comprising:
an illumination source that provides illumination light to a measurement site of an unfinished, multi-layer semiconductor wafer;
a spectrometer that detects light from the measurement site in response to the illumination light and generates a measured spectral response of the measurement site, the measured spectral response comprising measurement data; and
one or more computer systems configured to:
determine a structural characteristic of the unfinished, multi-layer semiconductor wafer based at least in part on the measurement data;
determine a dispersion metric associated with a layer of the unfinished, multi-layer semiconductor wafer based at least in part on the measurement data;
determine a band structure characteristic indicative of an electrical performance of a portion of the multi-layer semiconductor wafer based at least in part on the dispersion metric;
determine an estimate of one or more device performance metrics of the multi-layer semiconductor wafer, as if the unfinished, multi-layer semiconductor wafer were finished, based at least in part on the band structure characteristic and the structural characteristic;
determine an adjustment in one or more subsequent process steps based on a difference between the estimated values of the one or more device performance metrics and one or more corresponding specified final device performance values, wherein the adjustment includes a change in a targeted nominal process value of a subsequent process step; and
communicate an indication of the adjustment to a fabrication tool to perform the subsequent process step in accordance with the adjustment.

19. The system of claim 18, wherein the one or more computing systems is further configured to determine whether a device under process is expected to fall a final device performance test based on comparing the estimate of a device performance metric value and a specified final device performance value.

* * * * *